(12) United States Patent
Tournier

(10) Patent No.: US 9,033,946 B2
(45) Date of Patent: May 19, 2015

(54) DIAPER SHEATH

(75) Inventor: Gaëlle Tournier, Kowloon (HK)

(73) Assignee: PURE PRECISION LIMITED, Tortola (VG)

( * ) Notice: Subject to any disclaimer, the term of this patent is extended or adjusted under 35 U.S.C. 154(b) by 301 days.

(21) Appl. No.: 12/723,036

(22) Filed: Mar. 12, 2010

(65) Prior Publication Data

US 2011/0213326 A1     Sep. 1, 2011

(30) Foreign Application Priority Data

Feb. 26, 2010 (CN) .......................... 2010 1 0114228

(51) Int. Cl.
| | | |
|---|---|---|
| A61F 13/49 | (2006.01) | |
| A61F 13/493 | (2006.01) | |
| A61F 13/505 | (2006.01) | |
| A61F 13/15 | (2006.01) | |

(52) U.S. Cl.
CPC ......... *A61F 13/15268* (2013.01); *A61F 13/505* (2013.01)

(58) Field of Classification Search
CPC ............ A61F 13/496; A61F 13/49011; A61F 13/49017; A61F 13/505; A61F 13/49019; A61F 13/15268; A61F 13/49; A61F 13/565; A61F 13/49003; A61F 13/49058; A61F 13/15276; A61F 13/49061; A61F 13/49038; A61F 13/4906; A61F 13/68
USPC ............. 604/385.14, 385.15, 385.24–385.27, 604/385.3, 393–395
See application file for complete search history.

(56) References Cited

U.S. PATENT DOCUMENTS

| | | | |
|---|---|---|---|
| 2,085,913 A | 7/1937 | Lipton | |
| 2,664,895 A | 1/1954 | Shulman | |
| 2,969,065 A | 1/1961 | Fransworth | |
| 3,063,453 A | 11/1962 | Brecht | |
| 3,237,625 A | 3/1966 | Johnson | |

(Continued)

FOREIGN PATENT DOCUMENTS

| | | | |
|---|---|---|---|
| AU | 2007211915 B2 | 3/2008 | |
| CA | 2120840 A1 | 10/1995 | |

(Continued)

OTHER PUBLICATIONS

"The Natural Baby Company" GroBaby™ product description downloaded from the World Wide Web at www.thenaturalbabyco.com/gro-baby-i-54.htm dated Jan. 11, 2010, 3 pages.

(Continued)

*Primary Examiner* — Tan-Uyen (Jackie) T Ho
*Assistant Examiner* — Kathryn E Ditmer
(74) *Attorney, Agent, or Firm* — Miles & Stockbridge P.C.

(57) ABSTRACT

The present invention provide with a diaper sheath comprising: an inner and outer panel, each of said inner and outer panels having front and back portion connected by an intermediate portion, said front portion of the inner panel having an opening; and a front flap attached to said front portion of said inner panel, and said opening is covered by said front flap. The diaper of the present invention is much easier and convenient to adjust the insert from the opening at the front portion. With the flap at the front portion, parents can choose to use a biodegradable pad to insert in the flap and lay on the top of the inner panel.

8 Claims, 3 Drawing Sheets

(56) References Cited

U.S. PATENT DOCUMENTS

| | | | |
|---|---|---|---|
| 3,368,563 | A | 2/1968 | Scheier |
| 3,459,186 | A | 8/1969 | Schwartz |
| RE26,912 | E | 6/1970 | Scheier |
| 3,529,600 | A | 9/1970 | Seltzer |
| 3,530,859 | A | 9/1970 | Heimowitz |
| 3,613,687 | A | 10/1971 | Kennedy |
| 3,828,785 | A | 8/1974 | Gamm et al. |
| 4,402,690 | A | 9/1983 | Redfern |
| 4,411,660 | A | 10/1983 | Dawn et al. |
| 4,573,987 | A | 3/1986 | Lamb |
| 4,643,726 | A | 2/1987 | Gegelys |
| 4,704,117 | A | 11/1987 | Mitchell |
| 4,718,902 | A | 1/1988 | Bonito |
| 4,847,134 | A | 7/1989 | Fahrenkrug et al. |
| 4,938,753 | A | 7/1990 | Van Gompel et al. |
| 4,961,982 | A | 10/1990 | Taylor |
| 4,978,345 | A | 12/1990 | Holliday et al. |
| 5,078,709 | A | 1/1992 | Siciliano |
| 5,114,418 | A | 5/1992 | Levy |
| 5,197,958 | A | 3/1993 | Howell |
| 5,261,900 | A | 11/1993 | Houle et al. |
| 5,290,269 | A | 3/1994 | Heiman |
| 5,306,267 | A | 4/1994 | Hahn et al. |
| 5,368,585 | A | 11/1994 | Dokken |
| 5,389,093 | A | 2/1995 | Howell |
| 5,403,303 | A | 4/1995 | Beplate |
| 5,613,959 | A | 3/1997 | Roessler |
| 5,891,122 | A | 4/1999 | Coates |
| 6,155,083 | A | 12/2000 | Goeser et al. |
| 6,402,586 | B1 | 6/2002 | Winik et al. |
| 6,423,047 | B1 | 7/2002 | Webster |
| 6,579,273 | B2 | 6/2003 | Dupuy |
| 6,610,381 | B1 | 8/2003 | Conway |
| 6,705,128 | B1 | 3/2004 | Sciacca |
| 6,782,557 | B1 | 8/2004 | Feder |
| 6,806,214 | B2 | 10/2004 | Li et al. |
| 6,895,603 | B2 | 5/2005 | Coates |
| 7,438,707 | B2 | 10/2008 | Bushman et al. |
| 7,491,196 | B2 | 2/2009 | Franke et al. |
| 7,629,501 | B2 | 12/2009 | Labit et al. |
| 7,678,094 | B1 | 3/2010 | Cannon et al. |
| 7,686,796 | B2 | 3/2010 | Kuen et al. |
| 7,875,014 | B2 | 1/2011 | Hendren et al. |
| 7,914,507 | B1 | 3/2011 | Magee |
| 7,993,322 | B2 | 8/2011 | Brud et al. |
| 8,062,276 | B2 | 11/2011 | Labit et al. |
| 8,262,635 | B2 | 9/2012 | Labit et al. |
| 2001/0015600 | A1 | 8/2001 | Duong et al. |
| 2002/0010452 | A1 | 1/2002 | Dupuy |
| 2003/0181885 | A1 | 9/2003 | Harkness |
| 2004/0122392 | A1 | 6/2004 | Seneviratne |
| 2005/0148980 | A1 | 7/2005 | Fitton |
| 2005/0210560 | A1 | 9/2005 | Coates |
| 2006/0167432 | A1 | 7/2006 | Sigari |
| 2007/0277282 | A1 | 12/2007 | Sheppell |
| 2008/0065039 | A1 | 3/2008 | Labit et al. |
| 2008/0215027 | A1* | 9/2008 | Labit et al. ............ 604/378 |
| 2008/0215028 | A1 | 9/2008 | Brown et al. |
| 2009/0187156 | A1 | 7/2009 | Anzalone |
| 2009/0240228 | A1 | 9/2009 | Nonnenmann |
| 2010/0087794 | A1 | 4/2010 | Labit et al. |
| 2012/0172827 | A1* | 7/2012 | Dupuy ............ 604/378 |

FOREIGN PATENT DOCUMENTS

| | | |
|---|---|---|
| CN | 2 313 397 Y | 4/1999 |
| CN | 2479752 Y | 3/2002 |
| FR | 1 020 225 | 6/1950 |
| GB | 2452052 A | 2/2009 |
| GB | 2468724 A | 9/2009 |
| NZ | 549433 | 7/2008 |
| WO | WO 90/06066 A1 | 6/1990 |
| WO | WO 98/29080 A1 | 7/1998 |
| WO | WO 2008/030984 A2 | 3/2008 |

OTHER PUBLICATIONS

"Rump•a•rooz®" product description downloaded from the World Wide Web at www.rumparooz.com dated May 14, 2008, 3 pages.

"Rump•a•rooz®" G2 product description downloaded from the World Wide Web at www.rumparooz.com/catalog.php?category=65 dated Dec. 7, 2009, 3 pages.

"FuzziBunz™ Features" product description downloaded from the World Wide Web at www.fuzzibunzasia/fuzzi_details.php dated Apr. 6, 2009, 1 page.

"FuzziBunz™ One Size Diapers—Grows with Baby" product description downloaded from the World Wide Web at www.fuzzibunzasia/one_size_diaper.php dated Apr. 4, 2009, 1 page.

"Why Choose FuzziBunz™" description downloaded from the World Wide Web at www.fuzzibunzasia/why_choose_fuzzibunz.php dated Apr. 6, 2009, 1 page.

"Cotton Babies®" product description downloaded from the World Wide Web at www.cottonbabies.com/product_info.php?cPath=98&products_id=1279 dated Jan. 26, 2009, 7 pages.

Notification of the First Office Action date of dispatch Jun. 25, 2013, for Chinese Patent Application No. 201110286417.5 (and translation thereof).

Notification of Second Office Action date of dispatch Dec. 14, 2012, for Chinese Patent Application No. 201010114228.5 (and translation thereof).

EPO Communication dated Nov. 6, 2012, for European Patent Application No. 10707835.4.

Response to EPO Communication filed Mar. 18, 2013, for European Patent Application No. 10707835.4.

Response to EPO Communication filed Aug. 8, 2013, for European Patent Application No. 10707835.4.

Demand and amended claims filed with the EPO on Apr. 9, 2013, for PCT/EP2011/064882.

International Preliminary Report on Patentability date of completion Nov. 7, 2013, for PCT/EP2011/064882.

Written Opinion of the IPEA date of mailing Jul. 22, 2013, for PCT/EP2011/064882.

Amended claims filed with the EPO on Sep. 20, 2013, for PCT/EP2011/064882.

Office Action dated Dec. 16, 2013 for Australian Patent Application No. 2011218650.

Response to EPO Communication filed Mar. 23, 2012, in European Patent Application No. EP10707835.4.

Response to Chinese Office Action filed Aug. 21, 2012, in Chinese Patent Application No. CN201010114228.5 (and translation thereof).

* cited by examiner

DIAPER SHEATH

FIELD OF THE INVENTION

The present invention relates to a diaper sheath, and more particularly to a hybrid diaper.

BACKGROUND ART

On the present market, diapers for infants include the cloth diaper, the disposable diaper and the all-in-one diaper. As regards the diapers for infants, there are the health and sanitation issues, the energy and environment cost issues, as well as the economics involved in using each type.

As for use of the cloth diaper, frequent diaper changes are required in order to keep child dry and to help reduce infections such as diaper rash. Cloth diaper absorbs moisture, but it does not necessarily wick moisture away from the body. Thus, it becomes saturated very quickly. For preventing further spread of the moisture, outer waterproof covers or the so-called all-in-one diapers are used. Said all-in-one diaper combines itself with protective waterproof outer cover. With such covers or combinations, the parent cannot observe that the diaper is already wet. It has the same technical problem to the disposable diaper. Furthermore, said all-in-one diapers may also include absorbent disposable insert, which can be made of multiple layers of cotton or reusable pads.

As regards the diaper applied, other issue focuses on the comfort of the baby. In order to ensure retention and to prevent leakage but not so tight as to be uncomfortable or hamper blood circulation in the child's legs and to create high humidity or moisture within the diaper, the diaper has essentially to be snug. Said discomfortable or hampering of blood circulation in the child's legs are caused by elastic leg openings.

Further, hook and loop fasteners generally only allow for waist adjustment and do nothing for the leg openings.

Obviously the key issues are to ensure that the baby stays as dry and comfortable as possible and for as long as possible with the least bulk possible.

SUMMARY OF THE INVENTION

The aim of the present invention is to solve the above technical problem. According to the aim of the present invention, there is provided a diaper sheath comprising:

an inner and outer panels, each of said inner and outer panels having front and back portion connected by an intermediate portion, said front portion having an opening, each of said panels attached peripherally one to the other in matched contour;

front fastener attached to said front portion of said outer panel back fastener attached to back portion of said inner panel, said back fastener is cooperatively fastenable with said front fastener;

a front flap attached to said front portion of said inner panel, and said opening is covered by said front flat.

Preferably, said back portion of the inner panel having an opening.

Preferably, the diaper sheath comprising a back flap attached to said back portion of said inner panel.

Preferably, said back fastener attached to both ends of said back portion of said inner panel.

Preferably, said front fastener is front plurality of snaps, and said back fastener is back plurality of snaps; said back plurality of snaps is cooperatively fastenable with front plurality of snaps.

Preferably, the diaper sheath comprising: intermediate elastic strip attached to said inner and outer panels along each side of said intermediate portion.

Preferably, the diaper sheath comprising: intermediate button attached along each side of said intermediate portion, wherein said intermediate elastic strip has at least one intermediate hole cooperatively fastenable with intermediate button.

Preferably, the diaper sheath comprising back elastic strip attached to said inner and outer panels along the edge of said back portion.

Preferably, the diaper sheath comprising: back button attached along the edge of said back portion, wherein said back elastic strip has at least one back hole cooperatively fastenable with said back button.

Preferably, said inner and outer panels utilize a liquid permeable material; said inner face of said outer panel utilizes an impervious material.

Preferably, said inner panel is fleece material made of 100% polyester.

The present invention also provides a diaper comprising: a diaper sheath according to the present invention and a pad fully or partially inserted between said inner and outer panels.

Preferably, said pad is a removable, reusable, absorbent pad.

By means of the above technical solution, the present invention of diaper sheath has the technical effects as follows:

(1) The diaper sheath of the present invention is much easier and convenient to adjust the insert from the opening at the front portion.

(2) With the flap at the front portion, parents can choose to use a biodegradable pad to insert in the flap and lay on the top of the inner panel.

(3) With the fleece of the inner panel, the diaper sheath is extremely comfortable and perfect for the babies gentle new skin.

(4) With the elastic stripe and button, the parent can adjust the position of the elastic to fit their baby perfectly by simply changing the elastic position.

BRIEF DESCRIPTION OF THE DRAWINGS

For a further understanding of the nature and objects of the present invention, reference should be made to the following detailed description taken in conjunction with the accompanying drawings, wherein.

DETAILED DESCRIPTION OF THE PREFERRED EMBODIMENT

Embodiment 1

Figure 1:
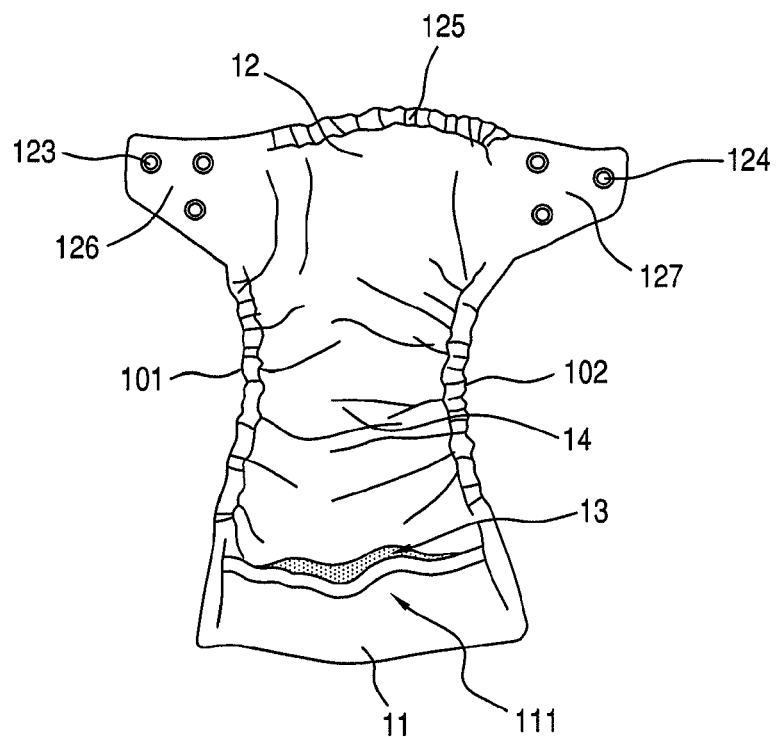
FIG. 1 is an inside view of the preferred diaper sheath embodiment 1.

The present sheath diaper is illustrated in FIG. 1 as viewed from the inside. The sheath diaper comprising:

inner and outer panels, each of said inner and outer panels having front and back portion 11, 12 connected by an intermediate portion 14, said front portion 11 of the inner panel having an opening 13, each of said panels attached peripherally one to the other in matched contour, said back portion 12 has two elongated wings 126, 127;

front plurality of snaps 112, 113, 114 attached to said front portion 11 of said outer panel back plurality of snaps 123, 124 attached to said two elongated wings 126, 127, said back plurality of snaps 123, 124 is cooperatively fastenable with said front plurality of snaps 112, 113, 114;

a front flap 111 attached to said front portion 11 of said inner panel, and said opening 13 is covered by said front flap 111. The legs have their own adjustment snaps. The waist also has its own set of snaps. The snaps are great for easy adjustment for the leg and for the waist.

Figure 2:
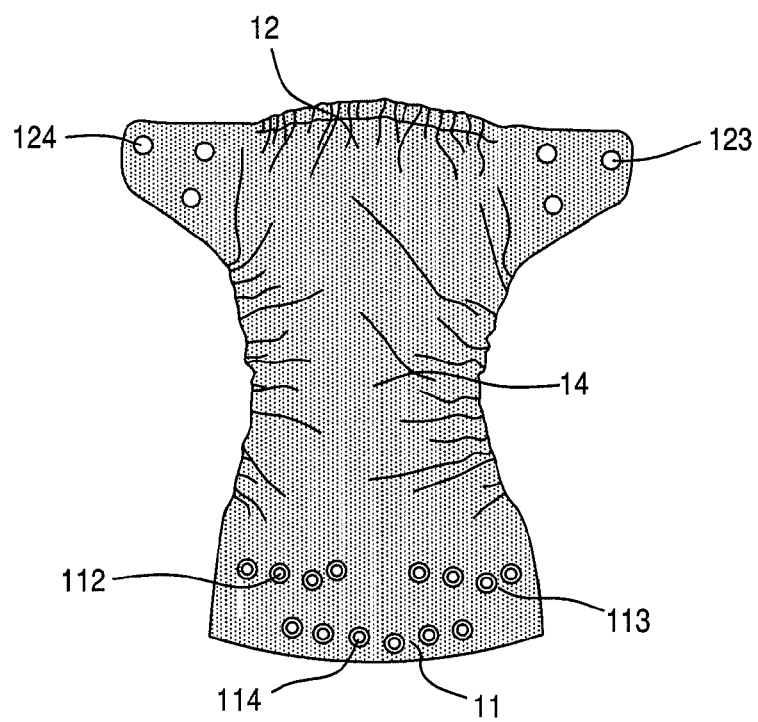
FIG. 2 is an outside view of the preferred diaper sheath embodiment 1.
Figure 3:
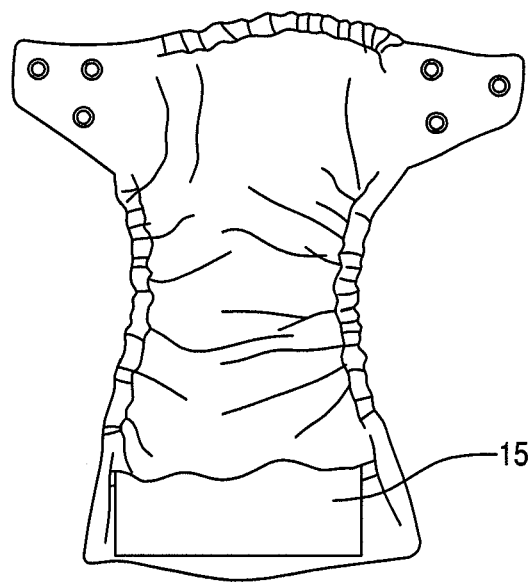
FIG. 3 is an inside view of the preferred diaper sheath embodiment 1 with a pad.

As shown in FIG. 1-3, the present diaper sheath comprises:

intermediate elastic strip 101, 102 attached to said inner and outer panels along each side of said intermediate portion 14;

back elastic strip 125 attached to said inner and outer panels along the edge of said back portion.

Said intermediate elastic strip 101, 102 and said back elastic strip 125 make the intermediate portion 14 and back portion 12 adjustable.

The diaper may further comprise: a removable, reusable, absorbent pad 15 fully or partially inserted between said inner and outer panels and located along said intermediate portion.

With the present diaper sheath, the parent may fill up the diaper sheath with one or two pads and close the opening 13 with said flap 111 at the front. It is much easier and convenient for the parent to adjust the insert from the front. Once the parent inserts the pad 15 in the diaper, they can adjust it perfectly from the front opening 13 to insure a perfect positioning. With the front pocket opening then they can easily adjust the pad 15 and put down the flap 111. This makes it ideal for adjustment while the baby is wearing it.

In the present embodiment, said inner panel utilizes a liquid permeable material, and said outer panel utilizes an impervious material. Said inner panel is fleece material made of 100% polyester, and said outer panel is plastic.

After repeated washes, the fabric will still be white and not stained, as said fabric is made of fleece. With the diaper sheath being washed and washed this is a major benefit. Parents can always be insured they have a nice clean looking diaper. We could use any other fabric like organic cotton, bamboo or others but do stain. However, fleece does not stain. Secondly, fleece is hypoallergenic making it perfect for babies gentle new skin.

Another added feature to the present invention is that with the flap 111 at the front, parents can choose to use a biodegradable pad 15 to insert in the flap 111 and lay on top of the fleece. With said added feature to use disposable pad 15, this makes it the perfect diaper. If the baby has stooled already and it is not expected that will occur in the next several hours when out, the disposable insert from the front becomes practicable and convenient for both boys and girls.

Embodiment 2

Figure 4:
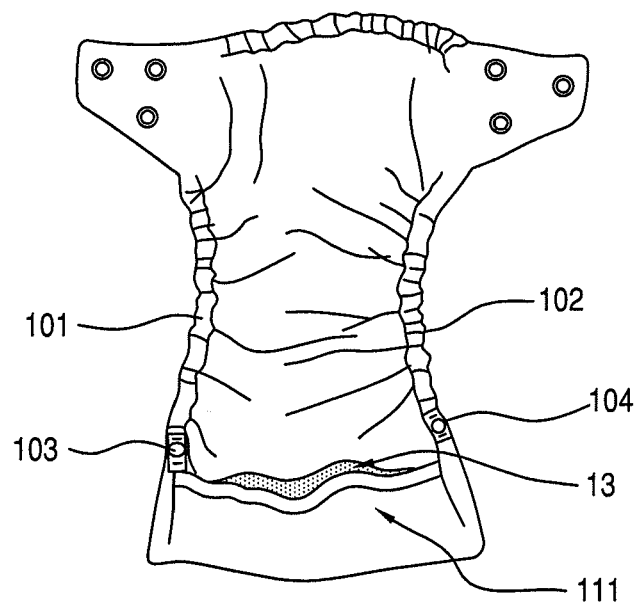
FIG. 4 is an inside view of the preferred diaper sheath embodiment 2.
Figure 5:
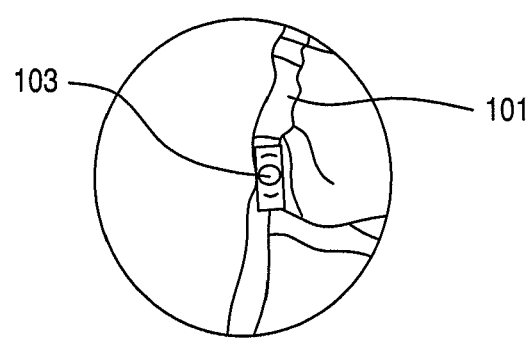
FIG. 5 is an additional figure of partial enlargement of the preferred diaper sheath embodiment 2.

As shown in FIGS. 4 and 5, the diaper sheath further comprising: intermediate buttons 103, 104 attached along each side of said intermediate portion 14, wherein said intermediate elastic strip 101 has at least one intermediate hole cooperatively fastenable with said intermediate button 103. The elastic stripes 101, 102 also have numbers that attach to 1 button at each side. The parents can adjust the position of the elastic strips 101, 102 to fit their baby perfectly by simply changing the elastic position.

The buttons 103, 104 is not removable which is safer and tidier. In addition, the buttons 103, 104 slips into the special opening 13 and disappear under the flap 111. It makes it invisible and does not touch the baby skin. With the numbers, the parent can recall the appropriate tightness each time and as and when the baby grows to adjust.

The diaper sheath of the present invention may further comprise back button attached along the edge of said back portion, wherein said back elastic strip has at least one back hole cooperatively fastenable with said back button.

In addition, the diaper sheath of the present invention may further comprise a back flap attached to said back portion of said inner panel. Because of the place where the opening 13 will be situate (not immediately at the top part of the diaper), there will less space for the pad 15 and hence holding it better. The back of the nappy will also be fully closed.

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in any limiting sense.

The invention claimed is:

1. A diaper sheath comprising:
inner and outer panels, each of said inner and outer panels having front and back portions connected by an intermediate portion, said front portion of the inner panel having an opening, each of said panels attached peripherally one to the other in matched contour;
a front fastener attached to said front portion of said outer panel;
a back fastener attached to said back portion of said inner panel, said back fastener being cooperatively fastenable with said front fastener;
a front flap attached to said front portion of said inner panel, and said opening being covered by said front flap;
an intermediate elastic strip attached to said inner and outer panels along each of two sides of said intermediate portion; and
an intermediate button attached along each said side of said intermediate portion,
wherein said intermediate elastic strip has at least one intermediate hole cooperatively fastenable with said intermediate button, and
wherein said buttons are attached to said intermediate portion where said opening meets said front flap such that, in a fastened state, said buttons are exposed from a surface side of the inner panel through the opening while not being enclosed between the outer panel and the inner panel.

2. The diaper sheath according to claim 1, wherein said back fastener is attached to both of two ends of said back portion of said inner panel.

3. The diaper sheath according to claim 1,
wherein said front fastener is a plurality of front snaps, and said back fastener is a plurality of back snaps, and
wherein said plurality of back snaps is cooperatively fastenable with said plurality of front snaps.

4. The diaper sheath according to claim 1, further comprising:
a back elastic strip attached to said inner and outer panels along an edge of said back portion.

5. The diaper sheath according to claim 4, wherein said inner panel comprises a liquid permeable material and said outer panel comprises a liquid impervious material.

6. The diaper sheath according to claim 4, wherein said inner panel comprises a fleece material made of 100% polyester.

7. A diaper comprising:
a diaper sheath according to claim 1, and
a pad fully or partially inserted between said inner and outer panels.

8. The diaper according to claim 7, wherein said pad is a removable, reusable, absorbent pad.

* * * * *